United States Patent [19]

Ito

[11] Patent Number: 4,971,035

[45] Date of Patent: Nov. 20, 1990

[54] INSERT PART OF ENDOSCOPE

[75] Inventor: Keiji Ito, Tokyo, Japan

[73] Assignee: Asahi Kogaku Kogyo Kabushiki Kaisha, Tokyo, Japan

[21] Appl. No.: 475,198

[22] Filed: Feb. 5, 1990

[30] Foreign Application Priority Data

Feb. 28, 1989 [JP] Japan .................... 1-47189

[51] Int. Cl.⁵ .............................. A61B 1/04
[52] U.S. Cl. ......................... 128/6; 358/98
[58] Field of Search ............... 128/4, 6; 358/98

[56] References Cited

U.S. PATENT DOCUMENTS

| | | | |
|---|---|---|---|
| 4,407,273 | 10/1983 | Ouchi | 128/6 |
| 4,730,909 | 3/1988 | Takahashi | 350/445 |
| 4,753,224 | 6/1988 | Tojo | 128/6 |
| 4,944,287 | 7/1990 | Takahashi | 128/4 |

Primary Examiner—William H. Grieb
Attorney, Agent, or Firm—Sandler, Greenblum & Bernstein

[57] ABSTRACT

A distal end part is connected to the distal end of a flexible tube, the distal end part having a larger outer diameter than that of the flexible tube. The distal end part has a substantially circular cross-sectional configuration that includes one or a plurality of flat peripheral portions. The distal end part is provided therein with an objective portion of an observation optical system which includes a solid-state image pickup device, for example.

10 Claims, 3 Drawing Sheets

INSERT PART OF ENDOSCOPE

BACKGROUND OF THE INVENTION

1. Field of the Invention

The present invention relates to an improvement in the structure of the insert part of an endoscope.

2. Description of the Related Art

The insert part of an endoscope that comprises a flexible tube and a distal end part connected to the distal end of the flexible tube must be as thin as possible in order to minimize the pain inflicted on the patient. In the present level of art, however, it is difficult to form a solid-state image pickup device, for example, a charge-coupled device (CCD), as thin as an image guide fiber bundle. In consequence, the distal end part that incorporates such a solid-state image pickup device is unavoidably thick to a certain extent.

If the flexible tube is formed thick in conformity with the distal end part, the pain inflicted to the patient increases. Since the signal cable of the solid-state image pickup device is not very thick, if the flexible tube is made thick, a useless space will be produced inside the tube.

Therefore, in the insert part of an endoscope that incorporates a solid-state image pickup device in the distal end portion thereof, it is preferable to form only the distal end part thick in comparison with the flexible tube, and the distal end part is commonly formed with a circular cross-sectional configuration.

However, the distal end part having a circular cross-sectional configuration becomes exceedingly thick when incorporating a solid-state image pickup device, so that great pain is inflicted on the patient when the distal end part passes through the patient's throat, for example. When the insert part is inserted into a bronchial tube, the distal end part clogs it and obstructs passage of air to the inner part of the bronchial tube.

SUMMARY OF THE INVENTION

An object of the present invention is to provide an insert part of an endoscope which is designed so that it can be smoothly inserted into the patient's body with minimized pains and it is possible to ensure the respiratory tract when it is inserted into a bronchial tube.

Other objects and advantages of the present invention will become apparent from the following detailed description of illustrated embodiments of the invention.

According to the present invention, there is provided an insert part of an endoscope comprising: a flexible tube; a distal end part connected to the distal end of the flexible tube, the distal end part having a larger outer diameter than that of the flexible tube and having a substantially circular cross-sectional configuration that includes one or a plurality of flat peripheral portions; and an objective portion of an observation optical system provided in the distal end part.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
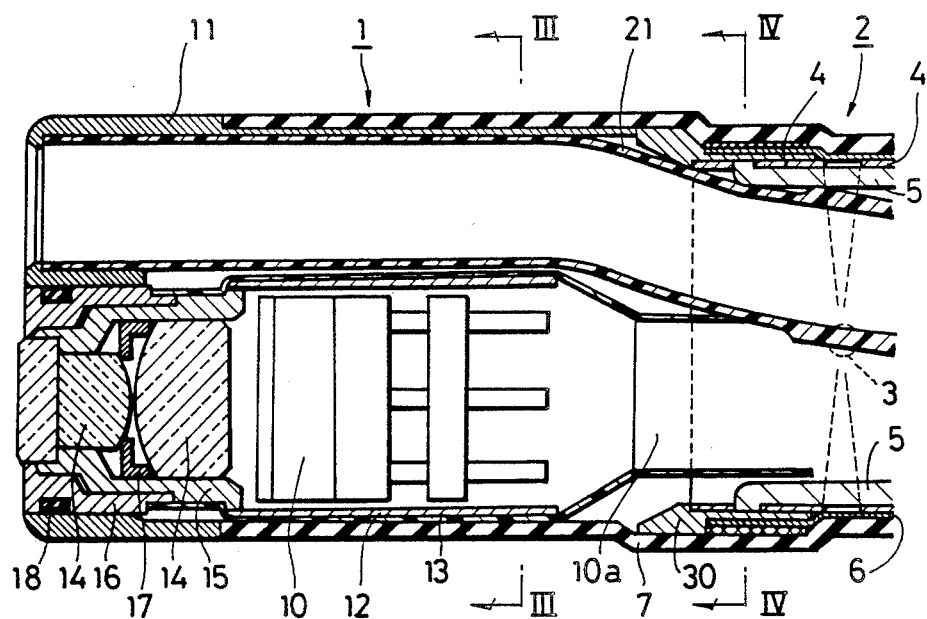
FIG. 1 is a sectional side view of the insert part of an endoscope according to a first embodiment of the present invention.
Figure 2:
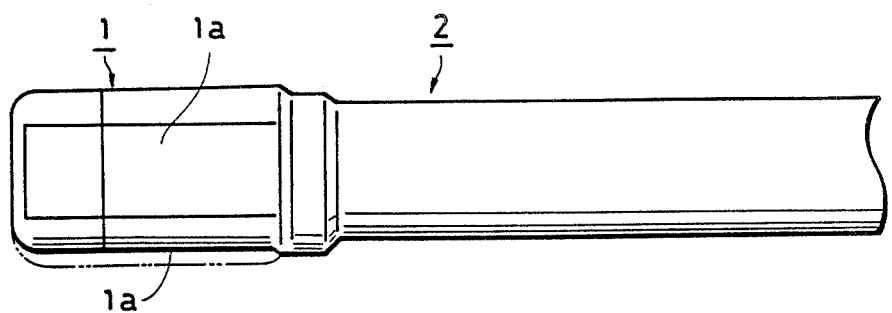
FIG. 2 is a side view of the insert part of the endoscope according to the first embodiment of the present invention.
Figure 3:
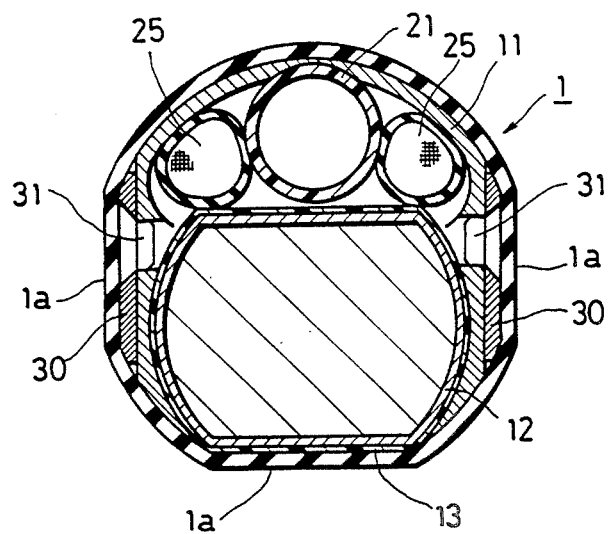
FIG. 3 is a sectional view taken along the line III—III of FIG. 1.
Figure 4:
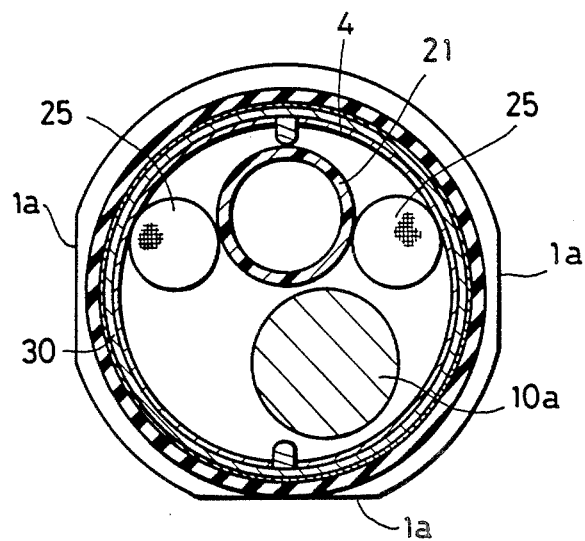
FIG. 4 is a sectional view taken along the line IV—IV of FIG. 1.

FIG. 1 is a sectional side view of the distal end portion of the insert part of an endoscope; FIG. 2 is a side view of the distal end portion of the insert part; and FIGS. 3 and 4 are sectional views taken along the lines III—III and IV—IV, respectively, of FIG. 1. The reference numeral 1 denotes a rigid distal end part. The reference numeral 2 denotes a bendable portion which can be bent by remote control and which is formed as being a part of a flexible tube which constitutes an insert part, the bendable portion 2 being provided at the distal end of the flexible tube. It should be noted that, although there are cases where the bendable portion 2 is not called a flexible tube, as being distinguished from the flexible tube portion, in the present invention the concept of "flexible tube" is interpreted broadly so as to include the bendable portion.

The reference numeral 4 denotes joint rings which are pivotally connected together by means, for example, of rivets 3. The reference numeral 5 denotes a bending control wire which is rigidly secured at one end thereof in a bore provided in the foremost joint ring 4 by means, for example, of silver-alloy brazing, the wire 5 being controlled by being pulled from a control part (not shown). The reference numeral 6 denotes a known braided-wire tube. The reference numeral 7 denotes a sheath made, for example, of an elastic rubber material.

The distal end part 1 is connected to the distal end of the bendable portion 2. The distal end part 1 has a substantially circular cross-sectional configuration with a larger outer diameter than that of the flexible tube portion including the bendable portion 2 because it accommodates an objective portion of an observation optical system that comprises a solid-state image pickup device 10 and objective lenses 14 and other built-in components.

However, since a signal cable 10a that is connected to the solid-state image pickup device 10 is much thinner than the solid-state image pickup device 10, the bendable portion 2 in which the signal cable 10a is inserted can be formed thin. Therefore, the distal end part 1 is formed so as to have a substantially circular cross-sectional configuration that includes three flat peripheral portions. More specifically, the periphery of a constituent material of the distal end part 1 that has a circular cross-section is cut in three directions so as to define three flat side surfaces each pair of adjacent ones of which are at 90° to each other. The reference numeral 1a denotes the flat surface portions. Each flat surface 1a is formed in parallel to the axis of the distal end part 1.

Thus, the useless portion of the distal end part 1 that is thick because it accommodates the solid-state image pickup device 10 is cut out and the outer diameter of the distal end part 1 is reduced correspondingly, so that the pain given to the patient when the insert part of the endoscope is inserted is relieved by a large margin.

The reference numeral 11 denotes a distal end part frame which defines the outer peripheral surface of the tip portion of the distal end part 1. A metallic frame 12 for securing the solid-state image pickup device 10 is secured inside the frame 11 through an insulating tape 13. As the solid-state image pickup device 10, for example, a charge-coupled device (CCD) is employed.

In front of the solid-state image pickup device 10 are disposed objective lenses 14 which are accommodated in a metallic lens frame 15. The lens frame 15 is secured to the distal end part frame 11 through an electrical insulator 16. The reference numerals 17 and 18 denote a spacer and an O-ring for sealing, respectively.

Thus, the image receiving surface of the solid-state image pickup device 10 is disposed so as to coincide with the imagery plane of the objective lenses 14, and an observed image that is formed on the image receiving surface is converted into an electric signal in the solid-state image pickup device 10. The frame 12 for the solid-state image pickup device 10 has a substantially circular cross-sectional configuration that includes two flat peripheral portions at the upper and lower sides, respectively, as viewed in FIG. 3. The distal end part 1 has a substantially circular cross-sectional configuration that includes three flat peripheral portions around the solid-state image pickup device 10, as stated above.

The reference numeral 21 denotes a forceps channel for insertion of forceps or other instruments used in endoscopic procedures which is disposed within the distal end part 1 in parallel to the frame 12 for the solid-state image pickup device 10. The wall thickness of the forceps channel 21 within the distal end part 1 is reduced with a view to minimizing the overall thickness of the distal end part 1. Since the forceps channel 21 is not bent within the distal end part 1, there is no fear of the channel 21 buckling even if the wall thickness thereof is reduced.

The upper edge portion of the distal end part 1 that extends along the forceps channel 21 has a circular cross-sectional configuration with no flat peripheral portion. In addition, light guide bundles 25 for illumination are disposed along both sides of the forceps channel 21, as shown in FIG. 3.

Referring back to FIG. 1, the reference numeral 30 denotes a metallic connecting tube that connects together the distal end part frame 11 and the joint rings 4 constituting the bendable portion 2. The rear end portion of the connecting tube 30 is fitted to the outer surface of the foremost joint ring 4 and secured thereto by means, for example, of soldering, as shown in FIG. 4. The forward end portion of the connecting tube 30 is disposed in such a manner as to clamp the distal end part frame 11 from both sides thereof and secured thereto by means of pins 31, as shown in FIG. 3. In this way, the distal end part 1 and the bendable portion 2 are connected together through the connecting tube 30.

Figure 5:
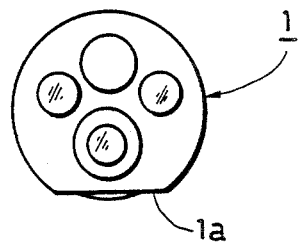
FIG. 5 is a front view of the insert part of an endoscope according to a second embodiment of the present invention.
Figure 6:
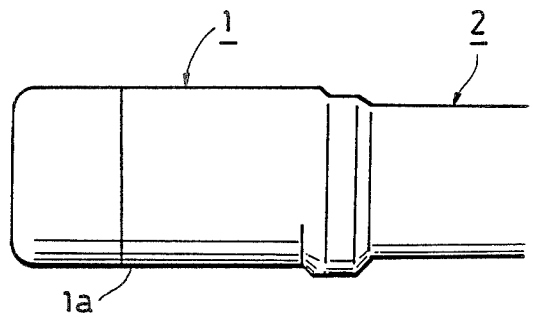
FIG. 6 is a side view of the insert part of the endoscope according to the second embodiment of the present invention.
Figure 7:
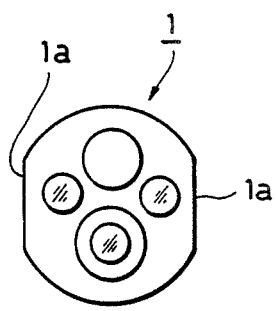
FIG. 7 is a front view of the insert part of an endoscope according to a third embodiment of the present invention.
Figure 8:
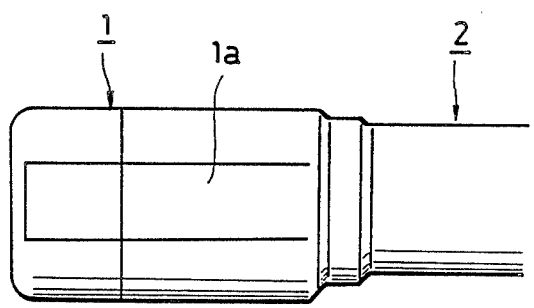
FIG. 8 is a side view of the insert part of the endoscope according to the third embodiment of the present invention.

FIGS. 5 and 6 show in combination a second embodiment of the present invention, in which the distal end part 1 has a substantially circular cross-sectional configuration that includes only one flat peripheral portion at the lower side thereof. FIGS. 7 and 8 show in combination a third embodiment of the present invention, in which the distal end part 1 has a substantially circular cross-sectional configuration that includes two flat peripheral portions at both sides thereof. The reference numeral 1a in these figures denotes the flat surface portions.

Thus, the distal end part 1 that has a larger outer diameter than the flexible tube is formed so as to have a substantially circular cross-sectional configuration that includes at least one flat peripheral portion, thereby enabling the pain inflicted on the patient to be relieved correspondingly to the reduction in the overall thickness of the distal end part 1.

According to the present invention, the thickness of the distal end part is reduced by an amount corresponding to a peripheral portion that would otherwise be present as in the case of the distal end part of the prior art that has a circular cross-sectional configuration with no flat peripheral portion. Accordingly, the distal end part can smoothly pass through the patient's throat, for example, so that the pain given to the patient is relieved. When it is inserted into a bronchial tube, the respiratory tract is satisfactorily ensured; therefore, the safety is also improved.

While the invention has been described by reference to specific embodiments chosen for purposes of illustration, it should be apparent that numerous modifications could be made thereto by those skilled in the art without departing from the basic concept and scope of the invention. For example, the present invention is also effectively applied to endoscopes that do not employ a solid-state image pickup device. More specifically, if the present invention is applied to an endoscope in which only the distal end part is thick because it incorporates an ultrasonic transducer or the like, the pain inflicted on the patient can be relieved in the same way as the above.

What is claimed is:

1. An insert part of an endoscope comprising:
   a flexible tube; and
   a distal end part connected to the distal end of said flexible tube, said distal end part having a larger outer diameter than that of said flexible tube and having a substantially circular cross-sectional configuration that includes at least one flat peripheral portion.

2. An insert part of an endoscope according to claim 1, wherein said flat peripheral portion is formed parallel to the axis of said distal end part.

3. An insert part of an endoscope according to claim 1, wherein an objective portion of an observation optical system is provided in said distal end part.

4. An insert part of an endoscope according to claim 3, wherein the objective portion of said observation optical system includes an objective lens and a solid-state image pickup device which converts a light image formed by said objective lens into an electric signal.

5. An insert part of an endoscope according to claim 4, wherein said solid-state image pickup device is a charge-coupled device (CCD).

6. An insert part of an endoscope according to claim 1, wherein said distal end part has a substantially circular cross-sectional configuration that includes three flat peripheral portions.

7. An insert part of an endoscope according to claim 1, wherein said distal end part has a substantially circular cross-sectional configuration that includes two flat peripheral portions.

8. An insert part of an endoscope according to claim 1, wherein said distal end part has a substantially circular cross-sectional configuration that includes one flat peripheral portion.

9. An insert part of an endoscope according to claim 1, wherein the distal end portion of said flexible tube is capable of being bent by remote control.

10. An insert part of an endoscope comprising:
a flexible tube;
a distal end part connected to the distal end of said flexible tube, said distal end part having a larger outer diameter than that of said flexible tube and having a substantially circular cross-sectional configuration that includes at least one flat peripheral portion which is formed in parallel to the axis of said distal end part; and
an objective portion of an observation optical system provided in said distal end part, said objective portion including an objective lens and a charge-coupled device (CCD) which converts a light image formed by said objective lens into an electric signal.

* * * * *